US006261773B1

(12) United States Patent
Segawa et al.

(10) Patent No.: US 6,261,773 B1
(45) Date of Patent: Jul. 17, 2001

(54) REAGENT FOR NUCLEIC ACID AMPLIFICATION AND PROCESS FOR NUCLEIC ACID AMPLIFICATION

(75) Inventors: Masaya Segawa; Motohiro Kondo; Yutaka Takarada, all of Otsu (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/268,710

(22) Filed: Mar. 16, 1999

(30) Foreign Application Priority Data

Mar. 17, 1998 (JP) .................................................. 10-066988
Jan. 27, 1999 (JP) .................................................. 11-018434

(51) Int. Cl.[7] .............................. C12Q 1/68; C12P 19/34
(52) U.S. Cl. .............................................. 435/6; 435/91.2
(58) Field of Search ........................................ 435/91.2, 6

(56) References Cited

U.S. PATENT DOCUMENTS 5,418,149 * 5/1995 Gelfand et al. ...................... 435/91.2

FOREIGN PATENT DOCUMENTS 88113948  8/1988 (EP) ................................ C12Q/1/68

OTHER PUBLICATIONS

Saiki, Randall K. et al., "Primer–directed Enzymatic Amplification of DNA with a Thermostable DNA Polymerase", *Science*, pp. 487–491 (1988).
Guatelli, John C. et al., "Isothermal, in vitro Amplifiction of Nucleic Acids by a Multienzyme Reaction Modeled After Retroviral Replication", *Proc. Nat'l. Acad. Sci. USA*, vol. 87, pp. 1874–1878 (1990).
Compton, J., "Nucleic Acid Sequence–Based Amplification", *Nature*, vol. 350, pp. 91–92 (1991).

Walker, G. Terrance et al., "Strand Displacement Amplification—An Isothermal, in vitro DNA Amplification Technique", *Nucleic Acids Research*, vol. 20, No. 7, pp. 1691–1696 (1992).
Abe, Chiyoji et al., "Detection of *Mycobacterium tuberculosis* is Clinical Speciments by Polymerase Chain Reaction and Gen–Probe Amplified *Mycobacterium Tuberculosis* Direct Test", *Journal of Clinical Microbiology*, vol. 31, No. 12, pp. 3270–3274 (1993).
Mueller, James D. et al., "Self–Sustained Sequence Replication (3SR): An Alternative to PCR", *Histochem Cell Biol*, 108:431–437 (1997).
Sambrook et al. Construction and analysis of cDNA libraries–molecular cloning, p. 8.11–8.17, 1989.*

* cited by examiner

Primary Examiner—W. Gary Jones
Assistant Examiner—Joyce Tung
(74) Attorney, Agent, or Firm—Kenyon & Kenyon

(57) ABSTRACT

The present invention provide a process for sequence-specific nucleic acid amplification capable of improving the detection sensitivity and increasing the signal. In particular, the present invention provides a reagent for nucleic acid amplification containing at least one member selected from the group consisting of EDTA, NTA, UDA, CyDTA, DTPA, GEDTA, TTHA and their salts, specifically a reagent for nucleic acid amplification comprising, in addition to the at least one compound, a forward primer having a DNA sequence homologous to a sequence of a target RNA; a reverse primer having a DNA sequence complementary to a sequence of the target RNA and having a promoter for RNA polymerase attached to its 5' end; ribonucleotides; deoxyribonucleotides; a reverse transcriptase or RNA-directed DNA polymerase; a RNase H; a DNA polymerase or a reverse transcriptase having DNA-directed DNA polymerase activity; and a RNA polymerase. The present invention also provides a process for nucleic acid amplification characterized by carrying out a nucleic acid amplification reaction in the presence of at least one member selected from the group consisting of EDTA, NTA, UDA, CyDTA, DTPA, GEDTA, TTHA and their salts.

10 Claims, 1 Drawing Sheet

SEQUENCE LISTING

<160> NUMBER OF SEQ ID NOS: 4

<210> SEQ ID NO 1
<211> LENGTH: 47
<212> TYPE: DNA
<213> ORGANISM: Artificial Sequence
<220> FEATURE:
<221> NAME/KEY: misc_binding
<222> LOCATION: (28)..(47)
<223> OTHER INFORMATION: DNA sequence complementary to a sequence of
      Mycobacterium tuberculosis 16S rRNA gene
<220> FEATURE:
<221> NAME/KEY: promoter
<222> LOCATION: (1)..(27)
<223> OTHER INFORMATION: promoter for T7 RNA polymerase

<400> SEQUENCE: 1
aattctaata cgactcacta tagggagcta cccgtcgtcg ccttggt                47

<210> SEQ ID NO 2
<211> LENGTH: 21
<212> TYPE: DNA
<213> ORGANISM: Artificial Sequence -continued

```
<220> FEATURE:
<221> NAME/KEY: misc_binding
<222> LOCATION: (1)..(21)
<223> OTHER INFORMATION: DNA sequence homologous to a sequence of
      Mycobacterium tuberculosis 16S rRNA gene

<400> SEQUENCE: 2
ggaaaggtct cttcggagat a                                          21

<210> SEQ ID NO 3
<211> LENGTH: 20
<212> TYPE: DNA
<213> ORGANISM: Artificial Sequence
<220> FEATURE:
<221> NAME/KEY: misc_binding
<222> LOCATION: (1)..(20)
<223> OTHER INFORMATION: DNA sequence complementary to a sequence of
      Mycobacterium tuberculosis 16S rRNA gene

<400> SEQUENCE: 3
taggaccacg ggatgcatgt                                            20

<210> SEQ ID NO 4
<211> LENGTH: 18
<212> TYPE: DNA
<213> ORGANISM: Artificial Sequence
<220> FEATURE:
<221> NAME/KEY: misc_binding
<222> LOCATION: (1)..(18)
<223> OTHER INFORMATION: DNA sequence complementary to a sequence of
      Mycobacterium tuberculosis 16S rRNA gene

<400> SEQUENCE: 4
gcgctttagc ggtgtggg                                              18
```

REAGENT FOR NUCLEIC ACID AMPLIFICATION AND PROCESS FOR NUCLEIC ACID AMPLIFICATION

FIELD OF THE INVENTION

The present invention relates to processes for nucleic acid amplification useful for biological research and clinical diagnosis, and reagents for use in the processes. More specifically, the present invention relates to processes for sequence-specific nucleic acid amplification which enable highly sensitive detection of nucleic acids, and reagents for use in the processes.

DESCRIPTION OF RELATED ART

In recent years, PCR (Polymerase Chain Reaction: Science, Vol. 239, pp. 487–491, 1988) and other techniques for artificially amplifying nucleic acids including DNA and RNA are widely known and utilized for medical and biological researches. The nucleic acid amplification techniques are indispensable for detection, cloning and modification of genes, and are finding wider application in clinical diagnosis. For example, a method for detecting pathogens with high sensitivity in a very short period has been developed and put into practical use, the method comprising amplifying a nucleic acid characteristic of a pathogen (e.g., Mycobacterium) and detecting the amplified nucleic acid. Also, application of the nucleic acid amplification techniques in detection of abnormalities of genes of humans and other animals is being researched for practical use.

In addition to PCR, a number of nucleic acid amplification techniques have been developed recently, which include LCR (Ligase Chain Reaction: Genomics 4, 560 (1989)), NASBA (Nucleic Acid Sequence-Based Amplification: Nature 350, p. 91 (1991)), SDA (Strand Displacement Amplification: Nucleic Acids Res. 20, 1961 (1992)), TMA (Transcription Mediated Amplification: J. Clin. Microbiol. 31, 3270 (1993)) and 3SR (Self Sustained Sequence Replication Reactions: Proc. Nat. Acad. Sci., USA 87, 1874–1878 (1990)).

Among these techniques, NASBA, TMA and 3SR are RNA amplification techniques wherein RNA is utilized as a target nucleic acid (template nucleic acid) for amplification.

The principle of these RNA amplification techniques is as follows. First, the target RNA is converted into a double-stranded DNA having a RNA promoter incorporated therein, using a DNA synthetase such as reverse transcriptase; and then 100 to 1,000 copies of RNA are obtained by transcription from the double-stranded DNA, using a RNA synthetase such as RNA polymerase. This cycle is repeated at a constant temperature to finally obtain several ten thousand to several million copies of the RNA.

Nucleic acid amplification techniques utilizing RNA as the target nucleic acid further include RT-PCR, which, however, involves the step of converting RNA into DNA by reverse transcription reaction, in advance of the PCR step. RT-PCR thus requires troublesome manipulations and much time (usually about 5 to 6 hours). In contrast, the other RNA amplification techniques mentioned above are advantageous in that they are simple and take less time since a series of reactions proceed in one operation.

Another future of these RNA amplification techniques is that the target RNA is amplified preferentially even if the sample contains DNA homologous to the target RNA. The RNA amplification techniques are therefore useful for, for example, precisely detecting or quantitating a desired RNA or the expression of a desired gene. On the other hand, amplification from contaminating DNA is inevitable in the PCR step of RT-PCR, resulting in a contaminated amplification product.

Further, these RNA amplification techniques, in particular NASBA, are characterized in that series of amplification reactions can be carried out at a constant temperature. Therefore, these techniques can be performed in a simple apparatus such as an ordinary constant temperature bath, instead of a thermal cycler.

Among these RNA amplification techniques, NASBA is characterized by high amplification efficiency. In an ideal reaction system of NASBA, the target RNA undergoes a rapid amplification reaction and gives a high positive signal if present beyond the detection limit, whereas it is not amplified and gives no signal if present below the detection limit. Accordingly, NASBA is beneficial in that it can give very clear positive/negative results.

Thus, these RNA amplification techniques are relatively advantageous from the viewpoints of operation simplicity and amplification efficiency.

However, nucleic acid amplification techniques, including the RNA amplification techniques and other techniques such as PCR, have a constant problem of non-specific amplification reactions. It is presumed that the non-specific amplification reactions occur mainly because primers will bind to non-target-nucleic acid sequences. Such reactions consume the primers and substrates (such as deoxyribonucleotide or ribonucleotide) and reduce the amplification efficiency of the target nucleic acid. Further, the presence of non-specific amplification reaction products in the amplification product decreases the detection signal from the amplified target nucleic acid and impairs the detection sensitivity.

For example, non-specific amplification reactions in PCR result in a reduced signal from the band corresponding to the desired amplification product and unclear electrophoresis profiles in the subsequent electrophoretic detection of the amplification product. Similar results are reached when the detection is carried out by other methods than electrophoresis, such as hybridization usually employed for NASBA product.

Occurrence of non-specific reactions greatly depends on properties of the primers used for amplification and selection of a sequence to be amplified. For preventing non-specific reactions, it is therefore necessary to select primers which are unlikely to cause non-specific reactions, taking into consideration the Tm value of the target nucleic acid and specificity and stereostructure of the sequence. However, selection of primers is often restricted since the sequence to be amplified is usually predetermined.

Studies have been made on a PCR method wherein non-specific reactions are reduced by controlling physical conditions such as temperature and period for annealing in each cycle and wherein the signal is improved by increasing the number of amplification cycles. Also reported is a two-step PCR method (nested PCR) wherein the detection sensitivity is improved by using a second pair of primers for synthesizing an internal region of the target sequence (J. Yourno et al., PCR Methods Applic. 2: 60 (1992)).

However, the former method is not applicable in NASBA and like techniques performed at a constant temperature, while the latter method requires complicated manipulations and thus greatly impairs the simpleness, an advantage of NASBA and like RNA amplification techniques.

SUMMARY OF THE INVENTION

An object of the invention is to provide a process for nucleic acid amplification which enables highly sensitive detection of a nucleic acid.

Another object of the invention is to provide an improved process for RNA amplification, specifically, an improved process for RNA amplification (in particular NASBA) wherein non-specific amplification reactions are significantly reduced to enable highly sensitive detection of a desired amplification product.

A further object of the invention is to provide a reagent for nucleic acid amplification for use in the above nucleic acid amplification process, preferably the improved process for RNA amplification, more preferably the improved process for NASBA.

A still further object of the invention is to provide a reagent kit useful for the above nucleic acid amplification process and for detection of the amplified nucleic acid.

The present inventors found that, when a specific compound such as ethylenediaminetetraacetic acid is added to a reaction mixture for nucleic acid amplification to carry out an amplification reaction in the presence of the compound, non-specific amplification reactions can be significantly inhibited, with the results that the desired amplification product can be detected as a high signal and that the detection sensitivity is markedly increased. The present invention has been accomplished based on this novel finding.

The present invention provides reagents described in the following Items 1 to 7:

1. A reagent for nucleic acid amplification containing at least one member selected from the group consisting of ethylenediaminetetraacetic acid, nitrirotriacetic acid, uramil diacetic acid, trans-1,2-cyclohexanediaminetetraacetic acid, diethylenetriamine-pentaacetic acid, ethylene glycol bis(2-aminoethyl)ether diaminetetraacetic acid, triethylenetetraminehexaacetic acid and their salts.

2. A reagent for nucleic acid amplification containing at least one member selected from the group consisting of ethylenediaminetetraacetic acid, nitrirotriacetic acid and their salts.

3. A reagent for nucleic acid amplification comprising a forward primer having a DNA sequence homologous to a sequence of a target RNA; a reverse primer having a DNA sequence complementary to a sequence of the target RNA and having a promoter for RNA polymerase attached to its 5' end; ribonucleotides; deoxyribonucleotides; a reverse transcriptase or RNA-directed DNA polymerase; a RNase H; a DNA polymerase or reverse transcriptase having DNA-directed DNA polymerase activity; a RNA polymerase; and at least one member selected-from the group consisting of ethylenediamine-tetraacetic acid, nitrirotriacetic acid, uramil diacetic acid, trans-1,2-cyclohexanediaminetetraacetic acid, diethylenetri-aminepentaacetic acid, ethyleneglycol bis(2-aminoethyl)ether diaminetetraacetic acid, triethylene-tetraminehexaacetic acid and their salts.

4. A reagent for nucleic acid amplification according to Item 3 further containing a buffer solution.

5. A reagent for nucleic acid amplification comprising a forward primer having a DNA sequence homologous to a sequence of a target RNA; a reverse primer having a DNA sequence complementary to a sequence of the target RNA and having a promoter for RNA polymerase attached to its 5' end; ribonucleotides; deoxyribonucleotides; a reverse transcriptase or RNA-directed DNA polymerase; a RNase H; a DNA polymerase or reverse transcriptase having DNA-directed DNA polymerase activity; a RNA polymerase; and at least one member selected from the group consisting of ethylenediamine-tetraacetic acid, nitrirotriacetic acid and their salts. This reagent may further contain a buffer solution.

6. A reagent for nucleic acid amplification according to any one of Items 1, 3 and 4 wherein the at least one member selected from the group consisting of ethylenediaminetetraacetic acid, nitrirotriacetic acid, uramil diacetic acid, trans-1,2-cyclohexanediamine-tetraacetic acid, diethylenetriaminepentaacetic acid, ethyleneglycol bis(2-aminoethyl)ether diaminetetraacetic acid, triethylenetetraminehexaacetic acid and their salts is used at a final concentration of 0.5 to 60 mM in the reaction mixture for nucleic acid amplification.

7. A reagent for nucleic acid amplification according to Item 2 or 5 wherein the at least one member selected from the group consisting of ethylenediamine-tetraacetic acid, nitrirotriacetic acid and their salts is used at a final concentration of 0.5 to 60 mM in the reaction mixture for nucleic acid amplification.

The present invention further provides processes for nucleic acid amplification described in the following Items 8 to 13.

8. A process for nucleic acid amplification characterized by carrying out a nucleic acid amplification reaction in the presence of at least one member selected from the group consisting of ethylenediaminetetraacetic acid, nitrirotriacetic acid, uramil diacetic acid, trans-1,2-cyclohexanediamine tetraacetic acid, diethylenetri-aminepentaacetic acid, ethyleneglycol bis(2-aminoethyl)ether diaminetetraacetic acid, triethylenetetraminehexaacetic acid and their salts.

9. A process for nucleic acid amplification characterized by carrying out a nucleic acid amplification reaction in the presence of at least one member selected from the group consisting of ethylenediaminetetraacetic acid, nitrirotriacetic acid and their salts.

10. A process for nucleic acid amplification according to Item 7 or 8 wherein the target nucleic acid to be amplified is RNA.

11. A process for nucleic acid amplification according to Item 7 or 8 wherein the nucleic acid amplification reaction is NASBA reaction.

12. A process for nucleic acid amplification according to Item 7 wherein the at least one member selected from the group consisting of ethylenediamine-tetraacetic acid, nitrirotriacetic acid, uramil diacetic acid, trans-1, 2-cyclohexanediaminetetraacetic acid, diethylenetri-aminepentaacetic acid, ethyleneglycol bis(2-aminoethyl)ether diaminetetraacetic acid, triethylene-tetraminehexaacetic acid and their salts is used at a final concentration of 0.5 to 60 mM in the reaction mixture for nucleic acid amplification.

13. A process for nucleic acid amplification according to Item 7 wherein the at least one member selected from the group consisting of ethylenediamine-tetraacetic acid, nitrirotriacetic acid and their salts is used at a final concentration of 0.5 to 60 mM in the reaction mixture for nucleic acid amplification.

The present invention further provides the reagent kits for amplification/detection of a nucleic acid described in the following Items 14 to 17.

14. A reagent kit for amplification/detection of a nucleic acid comprising a reagent for nucleic acid amplification according to Item 1 and a reagent for nucleic acid detection containing a detection probe.

15. A reagent kit for amplification/detection of a nucleic acid comprising a reagent for nucleic acid amplification according to Item 3 and a reagent for nucleic acid detection containing a detection probe.

16. A reagent kit for amplification/detection of a nucleic acid comprising a reagent for nucleic acid amplification according to Item 1 and a reagent for nucleic acid detection comprising a detection probe, a capture probe and an enzyme substrate.

17. A reagent kit for amplification/detection of a nucleic acid comprising a reagent for nucleic acid amplification according to Item 3 and a reagent for nucleic acid detection comprising a detection probe, a capture probe and an enzyme substrate.

DETAILED DESCRIPTION

Figure 1:
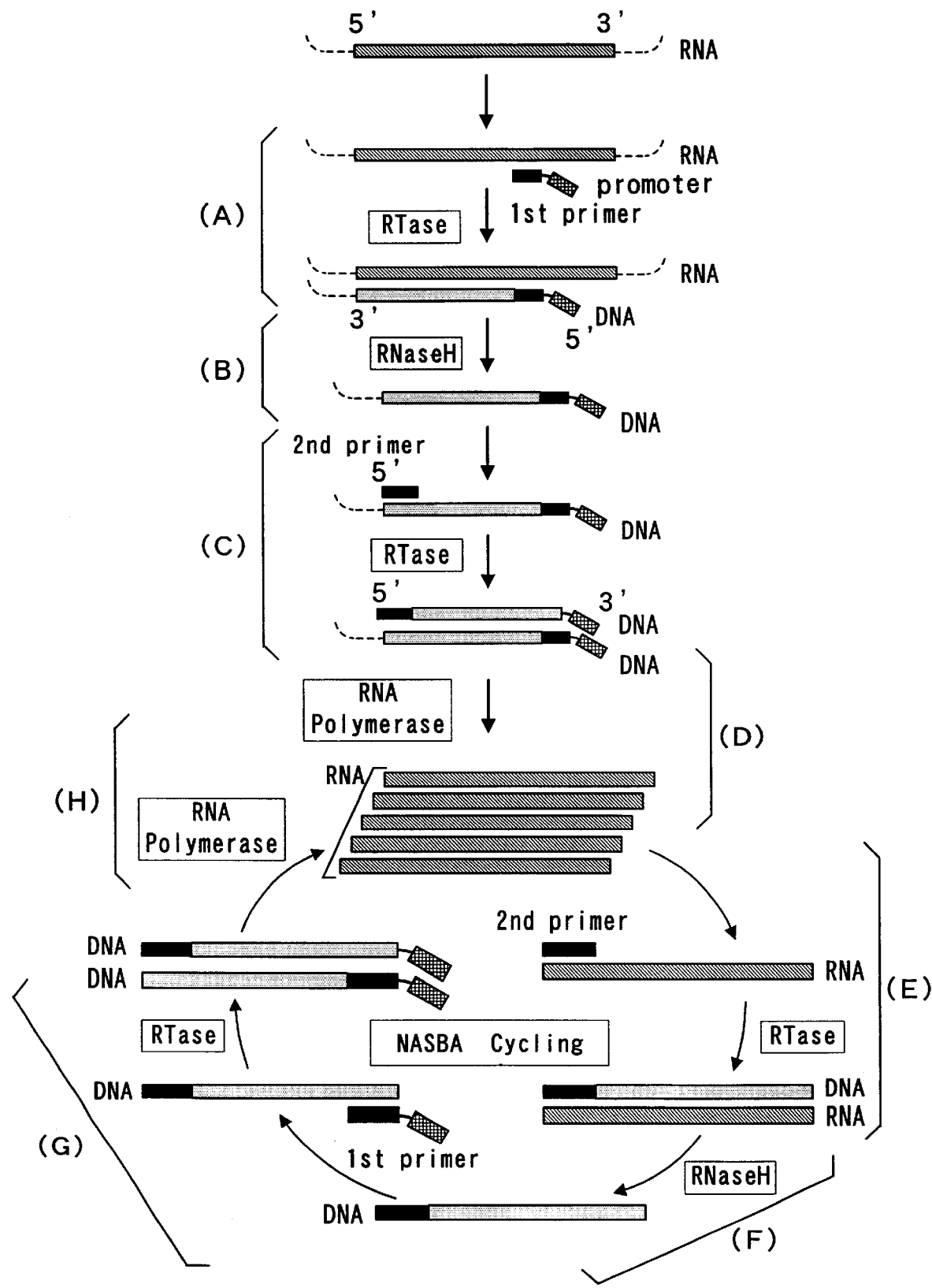
FIG. 1 shows the reaction steps of NASBA, which can be utilized to embody the process for nucleic acid amplification of the present invention. According to the invention, the reaction steps of NASBA are carried out in the presence of at least one member selected from the group consisting of ethylenediaminetetraacetic acid (EDTA), nitrirotriacetic acid (NTA), uramil diacetic acid (UDA), trans-1,2-cyclohexanediaminetetraacetic acid (CyDTA), diethylenetriaminepentaacetic acid (DTPA), ethyleneglycol bis(2-aminoethyl)ether diaminetetraacetic acid (GEDTA), triethylenetetraminehexaacetic acid (TTHA) and their salts.

The present invention provides a process for nucleic acid amplification wherein, among a number of nucleic acids present in a sample, a desired nucleic acid sequence (target nucleic acid sequence) is specifically amplified utilizing the complementarity of the target nucleic acid sequence, while inhibiting non-specific amplification reactions. In other words, the present invention provides an improvement on conventional processes for nucleic acid amplification. Specifically stated, the invention provides a process for nucleic acid amplification which enables highly sensitive detection of a nucleic acid, the process being capable of significantly inhibiting the occurrence of non-specific amplification reactions which has been a constant problem of conventional processes, whereby the amplified product can be detected as a high signal.

The process of the invention can be carried out by performing a nucleic acid amplification reaction in the presence of ethylenediaminetetraacetic acid (EDTA), nitrirotriacetic acid (NTA), uramil diacetic acid (UDA), trans-1,2-cyclohexanediaminetetraacetic acid (CyDTA), diethylenetriaminepentaacetic acid (DTPA), ethyleneglycol bis(2-aminoethyl)ether diaminetetraacetic acid (GEDTA), triethylenetetraminehexaacetic acid (TTHA), or a salt thereof. These compounds can be used singly or in combination.

Examples of useful salts include alkali metal salts such as sodium and potassium, and alkaline earth metal salts such as magnesium and calcium. Preferred are alkali metal salts such as sodium and potassium.

Among the above compounds, EDTA, NTA and their salts are preferable, and EDTA and its salts are more preferable. Preferred salts include alkali metal salts such as sodium and potassium.

Potassium salts are considered to be equivalent to sodium salts in inhibitory effect on non-specific reactions. However, potassium ions may affect reactions of various enzymes which participate in the nucleic acid amplification, and thus sodium salts are more desirable.

The concentration of the above compound for use in the nucleic acid amplification reaction is not limited, but usually about 0.5 to 60 mM, preferably 0.5 to 6 mM, as the final concentration in the reaction mixture.

Specifically stated, the process of the invention comprises adding the above compound to a reaction mixture for nucleic acid amplification and carrying out a nucleic acid amplification reaction using the resulting reaction mixture.

Examples of usable nucleic acid amplification reactions include PCR, NASBA, TMA, 3SR and other conventional nucleic acid amplification reactions. Among them, preferred are NASBA, TMA and 3SR and like RNA amplification reactions, among which NASBA is particularly preferred.

NASBA is a technique for amplifying a target single-stranded RNA using a forward and reverse primers and various enzymes, such as reverse transcriptase, DNA polymerase, ribonuclease and RNA polymerase, by which technique a specific RNA sequence between the two primers is amplified. Specifically stated, NASBA comprises the steps of synthesizing a single-stranded DNA having a sequence complementary to a sequence of a target single-stranded RNA, using the target single-stranded RNA as a first template for a first primer (reverse primer); synthesizing a double-stranded DNA using the obtained single-stranded DNA as a second template for a second primer (forward primer); and synthesizing a plurality of copies of RNA (amplification) using the obtained double-stranded DNA as a third template.

Usable as the first primer (reverse primer) is a primer which has a DNA sequence complementary to a 3'-end sequence of the first template RNA (target RNA) and which has a promoter for RNA polymerase attached to its 5' end. Usable as the second primer (forward primer) is a primer having a DNA sequence complementary to a 3' end sequence of the single-stranded DNA as the second template (i.e., a DNA sequence homologous to a 5= end sequence of the first template RNA (target RNA)).

When the present invention is applied in NASBA, the process of the invention comprises the following reaction steps performed in the presence of at least one compound selected from the group consisting of EDTA, NTA, UDA, CyDTA, DTPA, GEDTA, TTRA and their salts (see FIG. 1):

(A) In the presence of a reverse transcriptase or RNA-directed DNA polymerase, a first primer (reverse primer) is hybridized to a target RNA (first template) and allowed to extend along the target RNA sequence to obtain a RNA/DNA hybrid. As described above, the first primer has at its 3' end a DNA sequence complementary to a sequence of the target RNA and has a promoter for RNA polymerase, such as T7 promoter, attached to its 5' end.

(B) The RNA of the RNA/DNA hybrid is hydrolyzed using a ribonuclease having RNase H activity to obtain a single-stranded DNA.

(C) In the presence of a DNA polymerase or reverse transcriptase having DNA-directed DNA polymerase activity, a second primer (forward primer) is hybridized to the single-stranded DNA obtained in Step (B) and allowed to extend along the sequence of the single-strand DNA to obtain a double-stranded DNA. As describe above, the second primer has a DNA sequence complementary to a sequence of the single-stranded DNA. Since the single-stranded DNA has a sequence complementary to the target RNA sequence, the second primer has a sequence homologous to a sequence of the target RNA.

(D) A plurality of copies RNA are synthesized by transciption from the above double-stranded DNA using a RNA polymerase. The obtained RNA has a sequence complementary to the target RNA sequence.

(E) In the presence of a reverse transcriptase, i.e., a RNA-directed DNA polymerase, the second primer (forward primer) is reacted with the obtained RNA and allowed to extend along the sequence of the RNA to obtain a RNA/DNA hybrid.

(F) The RNA of the RNA/DNA hybrid is hydrolyzed using a ribonuclease having RNase H activity to obtain a single-stranded DNA.

(G) In the presence of a DNA polymerase or reverse transcriptase having DNA-directed DNA polymerase activity, the first primer (reverse primer) is reacted with the single-stranded DNA obtained in Step (F) and allowed to extend along the sequence of the single-stranded DNA to obtain a double-stranded DNA.

(H) A plurality of copies of RNA are obtained from the double-stranded DNA using a RNA polymerase.

(I) Steps (E) to (H) are repeated to synthesize a great number of copies of RNA having a sequence complementary to the target RNA sequence.

The above reaction steps can be carried out in a single reaction mixture (one-pot reaction) at a constant temperature, usually at about 37 to 45° C.

The present invention is applicable in not only NASBA, but also other nucleic acid amplification techniques which are conventionally employed or will be developed in the future, as long as the nucleic acid amplification reaction is carried out in the presence of at least one compound selected from the group consisting of EDTA, NTA, UDA, CyDTA, DTPA, GEDTA, TTHA and their salts.

The target RNA to be amplified according to the invention may be any RNA which one wishes to amplify, and is not limited by origin or the like. The target RNA can be obtained by isolating and purifying RNA of human body fluids (e.g., whole blood) or cultured cells in conventional manners (Maniatis, T et al.: Molecular Cloning, A Laboratory Manual, 7.3–7.36, Cold Spring Harbor Laboratory Press, 1989). For preparing RNA from bacteria culture, the bacteria are collected from the culture sample and washed, and RNA of the bacteria is adsorbed on silica particles in the presence of chaotropic ions (R. Boom et al.: Journal of Clinical Microbiology, Vol. 28, No. 3, p. 495, 1990).

The present invention also provides a reagent for nucleic acid amplification which enables highly sensitive detection of a nucleic acid, in particular a reagent for nucleic acid amplification capable of specifically amplifying a target nucleic acid sequence while significantly inhibiting non-specific amplification reactions.

The reagent for nucleic acid amplification of the invention basically comprises, in addition to a reagent conventionally used for nucleic acid amplification, at least one member selected from the group consisting of EDTA, NTA, UDA, CyDTA, DTPA, GEDTA, TTHA and their salts. The reagent of the invention is used preferably in RNA amplification techniques, particularly NASBA.

The reagent of the invention, when employed in RNA amplification techniques, particularly NASBA, may comprise at least (1) a reverse primer, (2) a forward primer, (3) ribonucleotides, (4) deoxyribonucleotides, (5) a reverse transcriptase or RNA-directed DNA polymerase, (6) a DNA polymerase or reverse transcriptase having DNA-directed DNA polymerase activity, (7) a ribonuclease, (8) a RNA polymerase and (9) at least one member selected from the group consisting of EDTA, NTA, UDA, CyDTA, DTPA, GEDTA, TTHA and their salts.

The ingredients of the reagent of the invention are described below.

(1) The reverse primer is an oligonucleotide having, at its 3' end, a DNA sequence complementary to a 3' end sequence of a target RNA (first template). Said DNA sequence (hereinafter referred to as "complementary sequence") has a promoter sequence for RNA polymerase attached to its 5' end. Further, the reverse primer may have a spacer sequence, where necessary. The promoter sequence is used for transcription from DNA to RNA in Step (A) of the amplification reaction.

The complementary sequence of the reverse primer can be selected according to the 3' end sequence of the target RNA to be amplified. The length of the sequence is not limited as long as it allows efficient DNA synthesis under given conditions, but is usually 15 to 25 bp. The promoter can be selected from a wide range according to the type of RNA polymerase for use in the RNA synthesis. Preferred examples include a promoter for T7 RNA polymerase.

(2) The forward primer is an oligonucleotide having a DNA sequence complementary to a 3' end sequence of the single-stranded DNA serving as a second template. In other words, the forward primer is an oligonucleotide having a sequence homologous to a 5' end sequence of the target RNA. Therefore, the DNA sequence of the forward primer can be selected according to the 5' end sequence of the target RNA, and may have a length of usually 15 to 25 pb.

Each of the reverse and forward primers can be used at a final concentration of about 0.05 to 1 $\mu$M, preferably about 0.2 $\mu$M in the reaction mixture for nucleic acid amplification.

(3) The ribonucleotides (rNTPs) may include adenosine 5'-triphosphate, guanosine 5'-triphosphate, uridine 5'-triphosphate and cytidine 5'-triphosphate. They can be used preferably at a final concentration of about 1.6 to 2.4 mM in the reaction mixture for nucleic acid amplification.

(4) The deoxyribonucleotides (dNTPs) may include deoxyadenosine 5'-triphosphate, deoxyguanosine 5'-triphosphate, deoxyuridine 5'-triphosphate and deoxycytidine 5'-triphosphate. They can be used preferably at a final concentration of about 0.8 to 1.2 mM in the reaction mixture for nucleic acid amplification.

(5) The reverse transcriptase or RNA-directed DNA polymerase may be any enzyme having an activity to synthesize DNA by extension of DNA from a primer using RNA as a template. The enzyme may further have DNA-directed DNA polymerase activity or RNase H activity, in addition to the above activity.

Examples of useful enzymes include avian myeloblastosis viral polymerase (AMV reverse transcriptase), Maloney murine leukemia viral polymerase (MMLV reverse transcriptase) and TthDNA polymerase. Other eukaryotic polymerases are also usable. Such an enzyme can be used at a final concentration of about 0.3 to 0.5 units/$\mu$l in the reaction mixture for nucleic acid amplification.

(6) The DNA polymerase or reverse transcriptase having DNA-directed DNA polymerase may be any enzyme having an activity to synthesize DNA by extension of DNA from a primer using DNA as a template. Preferred DNA polymerases are those free from 5'- or 3'-exonuclease activity, such as eukaryotic DNA polymerases (e.g., DNA polymerases α and β), DNA polymerases isolated from mammalian tissues such as calf thymus, Klenow fragment of E. Coli polymerase I, bacteriophage T7 DNA polymerase, Taq DNA polymerase, Pfu DNA polymerase, Vent DNA polymerase, KOD DNA polymerase and TthDNA polymerase. Preferred reverse transcriptases having DNA-directed DNA polymerase activity include AMV reverse transcriptase and MMLV reverse transcriptase. Such an enzyme can be used at a final concentration of about 0.1 to 1 unit/$\mu$l, preferably about 0.3 to 0.5 units/$\mu$l in the reaction mixture for nucleic acid amplification.

Preferred as the DNA polymerase or reverse transcriptase having DNA-directed DNA polymerase activity are TthDNA polymerase, AMV reverse transcriptase and MMLV reverse transcriptase, since they have the RNA-directed DNA polymerase activity described in (5), as well as the DNA polymerase activity, and can supply two activities by one enzyme. Among these preferred enzymes, AMV reverse transcriptase is particularly preferred for use in NASBA.

(7) The ribonuclease is not limited as long as it can selectively hydrolyze RNA annealed to a complementary DNA, without degrading the single-stranded RNA, double-stranded RNA and DNA. Specific examples include enzymes having RNase H activity such as E. coli RNase H, calf thymus RNase H and AMV reverse transpcriptase. The quantity of the ribonuclease to be used depends on the type of enzyme selected, but is usually about 0.0001 to 0.01 units/$\mu$l, preferably about 0.00025 unites/$\mu$l, as the final concentration in the reaction mixture for nucleic acid amplification.

Preferred ribonucleases include AMV reverse transcriptase, which has the RNA-directed DNA polymerase activity and DNA-directed DNA polymerase activity described in (5) and (6) as well as RNase H activity, and thus can supply three activities by one enzyme.

(8) The RNA polymerase may be any enzyme capable of binding to a particular DNA sequence called a promoter and to specifically initiate in vitro RNA synthesis at a initiation site in close proximity to the promoter. In addition, the RNA polymerase should be capable of synthesizing several copies of RNA per functional copy of the template in a reasonable time period. Examples of such enzymes include bacteriophage T7 RNA polymerase, phage T3 RNA polymerase, phage ¢ II RNA polymerase, Salmonella phage sp6 RNA polymerase, Pseudomonas phage gh-1 RNA polymerase and other prokaryotic or eukaryotic RNA polymerases. The RNA polymerase can be used at a final concentration of about 0.5 to 5 units/$\mu$l, preferably about 0.8 to 1.2 units/$\mu$l in the reaction mixture for nucleic acid amplification.

(9) EDTA, NTA, UDA, CyDTA, DTPA, GEDTA, TTHA and their salts may be used singly or in combination, in the reaction mixture for nucleic acid amplification. As mentioned above, usable salts include alkali metal salts such as sodium and potassium, and alkaline earth metal salts such as magnesium and calcium, among which alkali metal salts such as sodium and potassium are preferred. Of the above compounds, preferred are EDTA, NTA and their salts, and especially preferred are EDTA and its salts. Preferred salts are sodium salt and potassium salt, in particular sodium salt. The compound can be used at a final concentration of about 0.5 to 60 mM, preferably about 0.5 to 6 mM.

The reagent for nucleic acid amplification of the invention, which comprises the above primers, nucleotides, enzymes and compound such as EDTA, may further contain a buffer solution, metal ion or the like.

The buffer solution is not limited as long as it has buffer action at about pH 6 to 10. Buffer solutions for general purposes such as Tris-HCl are usable.

Examples of metal ions include magnesium ion and potassium ion. Magnesium ion or potassium ion, when employed, is used preferably at a final concentration of about 10 to 14 mM or about 56 to 84 mM, respectively, in the reaction mixture for nucleic acid amplification, although these values are not limitative.

According to the present invention, the above ingredients need not be provided in the form of a mixture, as long as they can be used in a single reaction mixture at the time of amplification of a target nucleic acid. That is, the above ingredients (1) to (9), together with the optional buffer solution and/or metal ions, may be packaged together in the form of a single solution mixture, or alternatively the enzymes and the other ingredients may be separately packaged and provided as a reagent kit.

Generally, nucleic acid amplification techniques are utilized to precisely detect a target nucleic acid present in a trace amount in a sample. The process for nucleic acid amplification using the reagent of the present invention makes it possible to detect, with high sensitivity, an amplified target nucleic acid as a high signal.

Accordingly, the present invention also provides a reagent kit for amplification/detection of a nucleic acid, the reagent kit comprising the reagent for nucleic acid amplification and a reagent for detecting the target nucleic acid amplified by the nucleic acid amplification reaction (hereinafter referred to as "reagent for nucleic acid detection").

Conventional techniques for detecting an amplified nucleic acid include (i) electrophoresis; (ii) a technique comprising adding a labeled precursor to an amplification reaction mixture, and qualitatively or quantitatively determining the amplified nucleic acid labeled with the labeled precursor, using the label as an index; and (iii) a technique comprising immobilizing an amplified nucleic acid on a solid phase support, hybridizing the immobilized nucleic acid to a detection probe having a sequence complementary to the immobilized nucleic acid sequence, removing unhybridized detection probe, and qualitatively or quantitatively determining the amplified nucleic acid labeled with the detection probe using the label as an index.

The reagent for nucleic acid detection may comprise various ingredients according to the technique to be employed for detection of the amplified nucleic acid.

For example, the labeled precursor for use in the technique (ii) may be a labeled ribonucleoside triphosphate for detecting amplified RNA, or a labeled deoxynucleoside triphosphate or oligonucleotide primer for detecting amplified DNA. The label may be a radioisotope; a chemical substance such as biotin, chromophore, fluorochrome, or hapten which binds to an antibody; or a protein or enzyme.

The amplified nucleic acid labeled with the labeled precursor can be easily selected by hybridizing it to an immobilized nucleic acid having a sequence complementary to the labeled nucleic acid sequence, and can be detected by utilizing the label provided by the precursor.

The detection probe for use in the technique (iii) may be an oligonucleotide having a sequence complementary to the amplified nucleic acid sequence, so that the probe binds to the amplified nucleic acid. The complementary sequence can be prepared based on part of the target nucleic acid sequence, specifically, part of the sequence between the first and second primers. It is preferable that the detection probe be labeled for facilitating the detection. The label may be radioisotope; a chemical substance such as biotin, avidin, chromophore, fluorochrome, or hapten which binds to an antibody; a protein or enzyme such as phosphatase or peroxidase.

Useful solid phase supports include those conventionally employed in the art, such as a microtiter plate.

A capture probe can be immobilized on the solid phase support in order to capture and immobilize the amplified nucleic acid. The capture probe, like the detection probe, may be an oligonucleotide having a sequence complementary to the amplified nucleic acid sequence, so that the capture probe binds to the amplified nucleic acid. The complementary sequence can be prepared based on part of the target nucleic acid sequence, specifically, part of the sequence between the first and second primers. The capture probe contains a binding group for binding to the solid phase support. Examples of such binding groups include biotin. For instance, when the capture probe contains biotin as the binding group, it binds to and is immobilized on the solid phase support via avidin or streptavidin fixed on the solid phase support. The amplified target nucleic acid is captured by the capture probe immobilized on the solid phase support, and then treated with the detection probe to sandwich it between the capture and detection probes, followed by determination using the label of the detection probe as an index.

Alternatively, when biotin or like chemical group is introduced into the target nucleic acid during the amplification process, the amplified target nucleic acid can be immobilized on the solid phase support via avidin or streptavidin fixed on the solid phase support, without using the capture probe.

Therefore, the reagent for nucleic acid detection in the reagent kit for amplification/detection of a nucleic acid of the invention may comprise any of the above mentioned labeled precursor, detection probe, capture probe and the like, according to the detection technique employed. The reagent for nucleic acid detection may further contain, for example, an enzyme substrate or the like, according to the label used for the detection probe. The reagent for nucleic acid detection preferably comprises a detection probe, capture probe, and enzyme substrate suitable to the label used for the detection probe, and may further contain various solutions such as a washing solution, diluent and reaction terminating solution, and accessories such as a solid phase support (e.g., microtiter plate) and dropping pipette.

EXAMPLES

Embodiments of the present invention are shown below in the form of working examples to illustrate the present invention and its effects in further detail. These examples, however, are in no way limitative of the scope of the invention.

Example 1

Amplification of Mycobacterium tuberculosis 16S rRNA using amplification reaction mixture containing EDTA, and detection of amplified RNA (1) Synthesis of DNA primers for amplification of Mycobacterium tuberculosis 16S rRNA An oligonucleotide of SEQ. ID. NO. 1 (a reverse primer for amplification of Mycobacterium tuberculosis 16S rRNA; hereinafter referred to as Primer 1) and an oligonucleotide of SEQ. ID. NO. 2 (a forward primer for amplification of Mycobacterium tuberculosis 16S rRNA; hereinafter referred to as Primer 2) were synthesized by the phosphoamidite method using DNA Synthesizer Model 392 (Perkin-Elmer).

Primer 1 had at its 3' end a DNA sequence (20 nucleotides) complementary to a 3' end sequence of the target RNA, and had a T7 promoter sequence (27 nucleotides) attached to its 5' end. Primer 2 had a DNA sequence (21 nucleotides) homologous to a 5' end sequence of the target RNA.

These oligonucleotides were synthesized according to the manufacture's instructions on the synthesizer, deprotected in aqueous ammonia at 55° C. overnight, and purified through an anion exchange column using FPLC (Pharmacia).

(2) Preparation of capture probe and detection probe

An oligonuclotide of SEQ. ID. NO. 3 and an oligonucleotide of SEQ. ID. NO. 4 were synthesized by the phosphoamidite method using DNA Synthesizer Model 392 (Perkin-Elmer) according to the manufacturer's instructions. The oligonuclotide of SEQ. ID. NO. 3 was used as a capture probe for detecting a NASBA product of Mycobacterium tuberculosis 16S rRNA (hereinafter referred to simply as "capture probe"), and the oligonucleotide of SEQ. ID. NO. 4 was used as a detection probe for detecting the NASBA product of Mycobacterium tuberculosis 16S rRNA (hereinafter referred to simply as "detection probe").

Subsequently, a linker arm was attached to the oligonucleotide for capture probe (SEQ. ID. NO. 3) by replacing thymine at the 5' end with uridine having at the 5-position a linker arm containing an amino group as a reactive group. Uridines having a linker arm at the 5-position can be chemically synthesized from deoxyuriedine by the method described in WO/84/03285.

A linker arm was also attached to the oligonucleotide for detection probe (SEQ. ID. No. 4) by replacing thymine as the fifth base from the 5' end with uridine having a linker arm.

The synthesized oligonucleotides with linker arm (capture and detection probes with linker arm) were treated with aqueous ammonia at 50° C. overnight for deprotection, and purified through an anion exchange column using FPLC (Pharmacia) for use in subsequent steps.

(3) Binding of capture probe to microtiter plate

The capture probe with linker arm synthesized in (2) was bound to the inner surface of a microtiter plate via the linker arm.

Specifically stated, the capture probe with linker arm was diluted with a borate buffer (pH 10) containing 100 mM $MgCl_2$ to obtain a solution of 0.05 pmol/$\mu$l capture probe. 100 $\mu$l of the resulting solution was poured into each well of a microtiter plate (MicroFLUOR B; Dynatech), and allowed to stand at room temperature for about 15 hours to bind the capture probe to the inner surfaces of the wells via the linker arm. The solution in the wells was replaced with a solution containing 0.1 pmol dNTP, 0.5% polyvinylpyrrolidone (PVP) and 5× SSC (Standard Saline Citrate), which was then allowed to stand at room temperature for about 2 hours in order to prevent non-specific reactions in the following steps. Subsequently, the wells were washed with 1× SSC and dried.

(4) Enzyme labeling of detection probe

Alkaline phosphatase was bound to the detection probe synthesized in (2) via the linker arm, by following the method described in Nucleic Acid Res.: Vol. 14, p. 6115, 1986.

Specifically stated, the alkaline phosphatase was bound by the following procedure. First, the detection probe with linker arm ($A_{260}$=1.5) was dissolved in 12.5 $\mu$l of 0.2M $NaHCO_3$. To the solution was added 25 $\mu$l of a solution of 10 mg/ml disuccinimidyl suberate (DSS) to carry out reaction at room temperature for 2 minutes. The reaction mixture was subjected to gel filtration through a Sephadex G-25 column (1 cm in diameter and 30 cm in length; Pharmacia) equilibrated with 1 mM $CH_3COONa$ (pH 5) to remove excess DSS. The detection probe with linker arm, in which the amino group at the end of the linker arm had been activated, was reacted with double the molar quantity of alkaline phosphatase (Bellinger-Mannheim; used as dissolved in a solution containing 100 mM $NaHCO_3$ and 3M NaCl) at room temperature for 16 hours to thereby obtain an alkaline phosphatage-labeled detection probe. The labeled detection probe was purified by anion exchange column chromatography (FPLC; Pharmacia). The fraction containing the labeled detection probe was collected, and concentrated by ultrafiltration using Centricon 30K (trade name, a product of Amicon).

(5) Preparation of RNA sample containing target RNA (Mycobacterium tuberculosis 16S rRNA)

RNA was extracted from a culture sample of Mycobacterium tuberculosis by the method of R. Boom et al. (Journal of Clinical Microbiology: Vol. 28, No. 3, p. 495, 1990), and diluted to prepare RNA solutions of three different concentrations: 0.1 pg/µl, 1 pg/µl and 10 pg/µl. A yeast RNA extracted from yeast by the above method was added as a negative RNA to each RNA solution at a concentration of 10 ng/µgl.

(6) Amplification of Mycobacterium tuberculosis 16S rRNA

Using the RNA solutions prepared in (5) as RNA samples, the target RNA (Mycobacterium tuberculosis 16S rRNA) was amplified. Primers 1 and 2 prepared in (1) were used as a reverse primer and forward primer, respectively. The amplification reaction was carried out in the presence of EDTA-Na by using reaction mixtures containing EDTA-Na at various concentrations (0.5 mM, 1.0 mM, 1.5 mM and 3.0 mM). As a comparative experiment, an amplification reaction was carried out in the same manner except for using a reaction system lacking in EDTA-Na. The above amplification reactions were performed basically by following the procedure and conditions for NASBA described in Nature, Vol. 350, p.91, 1991. The publication is incorporated herein by reference.

Specifically stated, 5 µl of the RNA sample was mixed with 10 µl of a solution containing the ingredients other than enzymes (i.e., Primers 1 and 2, EDTA-Na, ribonucleotides and deoxyribonucleotides), followed by incubation at 65° C. for 5 minutes for denaturing the RNA. Then, 5 µl of an enzyme mixture (0.4 units of AMV reverse transcriptase, 0.00025 units of E. coli RNase H, 1 unit of E. coli RNA polymerase, 12 mM $MgCl_2$, 70 mM KCl and 40 mM Tris-HCl (pH 8.5)) to carry out a reaction at 41° C. for 90 minutes.

The above reaction amplified the antisense RNA sequence (a RNA sequence complementary to the target RNA sequence) between Primers 1 and 2.

(7) Detection of amplified RNA (Mycobacterium tuberculosis 16S rRNA)

-Sandwich hybridization on microtiter plate-

The amplification reaction mixture obtained in (6) was diluted tenfold and added to 0.3N NaOH to denature the amplified RNA. 20 µl of the resulting mixture was added to 100 µl of a solution consisting of 200 mM citrate-phosphate buffer (pH 6.0), 2% Sucraph AG (trade name, a product of Nippon Fine Chemical Co., Ltd.), 750 mM NaCl and 0.1% $NaN_3$. The resulting solution was poured into the wells of the microtiter plate supporting the capture probe and prepared in (3), and liquid paraffin was layered over the solution to prevent evaporation. Then, the microtiter plate was shaken at 50° C. for 30 minutes, so that RNA amplified from Mycobacterum tubercolosis 16 S rRNA was specifically captured by the capture probe immobilized on the microtiter plate.

Thereafter, the solution in the wells was replaced with a solution (5×SSC (pH 7.0), 0.1% Sucraph AG (a product of Nippon Fine Chemical Co., Ltd.), 0.5% PVP, 10 mM $MgCl_2$, 1 mM ZnCl and 0.1% $NaN_3$) containing 2 fmol/µl alkaline phosphatase-labeled detection probe prepared in (4), and liquid paraffin was layered over the solution to prevent evaporation. The microtiter plate was then shaken at 50° C. for 30 minutes, so that the alkaline phosphatase-labeled detection probe specifically bound to the RNA captured by the capture probe. Then, the solution in the wells was replaced with a solution containing 2×SSC (pH 7.0) and 0.1% Sucraph AG, which was then maintained at 50° C. for 10 minutes and further replaced with 1×SSC for washing the wells. After removing the washing solution, 100 µl of a dioxetane compound (trade name "Lumiphos 480"; Lumigen), i.e., a luminescence substrate of alkaline phosphatase, was poured into the wells and maintained at 37° C. for 15 minutes. Then, luminescence quantity was measured with a photon counter (Hamamatsu Photonics) in a dark room.

All the above steps can be carried out automatically by the DNA probe automatic measuring system (Journal of Japan Society for Clinical Laboratory Automation, Vol. 20, p. 728, 1995). The publication is incorporated herein by reference. The time required for the amplification and detection of the nucleic acid was about 2 hours.

(8) Results (Effect of addition of EDTA)

Table 1 shows the results of detecting, by the method (7), Mycobacterium tuberculosis 16S rRNA amplified by the method (6) using an EDTA-containing reaction mixture, in the presence of a negative RNA (10 ng/µl yeast RNA) (n=4). The numeric values in the table indicate luminescence quantities (cps, count/second).

TABLE 1

| Concentration of Mycobacterium RNA | EDTA concentration in reaction mixture for NASBA of Mycobacterium tuberculosis 16S rRNA | | | | |
|---|---|---|---|---|---|
| | 0 | 0.5 mM | 1.0 mM | 1.5 mM | 3.0 mM |
| 10 pg/µl | 18,546 | 65,342 | 111,325 | 153,264 | 120,339 |
| | 18,222 | 44,596 | 105,826 | 148,221 | 116,705 |
| | 15,431 | 43,121 | 99,256 | 124,406 | 98,456 |
| | 12,426 | 41,333 | 84,325 | 115,555 | 92,643 |
| 1 pg/µl | 5,846 | 5,152 | 45,216 | 86,972 | 55,260 |
| | 1,236 | 5,023 | 41,265 | 83,215 | 45,564 |
| | 959 | 4,210 | 35,168 | 65,413 | 33,216 |
| | 454 | 2,516 | 12,568 | 44,159 | 19,845 |
| 0.1 pg/µl | 525 | 125 | 1,526 | 20,012 | 11,826 |
| | 103 | 91 | 126 | 5,421 | 246 |
| | 76 | 85 | 97 | 96 | 72 |
| | 69 | 59 | 76 | 82 | 66 |

The results reveal that the luminescence quantity (positive signal) is remarkably increased by addition of EDTA-Na to the reaction mixture. Although addition of 0.5 mM EDTA-Na exhibits significant effect, higher concentrations are preferable, and concentrations about 1.5 mM are optimal. Addition of 1.5 mM EDTA-Na increases the positive signal 6- to 12-fold when the initial concentration of the target RNA is 10 pg/µl, and 8- to 20-fold when the initial concentration is 1 pg/µl, as compared with the positive signal obtained without using EDTA-Na. In conventional systems for nucleic acid detection, an initial concentration of 1 pg/µl is considered to be a detectable level, but the actual detection result is sometimes negative owing to a low signal. When the initial concentration is as low as 0.1 pg/µl, the target DNA cannot be detected at all. Therefore, the detection limit in conventional detection systems is about 1 pg/µl.

In contrast, when the reaction system contains EDTA-Na according to the invention, the positive signal significantly increases. As the result, an initial concentration of 1 pg/µl is a perfectly detectable level, and a positive signal can be detected even when the initial concentration is 0.1 pg/µl. Accordingly, the detection limit (the initial concentration of the target RNA) according to the present invention is about 0.1 pg/µl. That is, the present invention improves the detection sensitivity of conventional detection techniques about tenfold.

Consequently, when EDTA is used in amplification of Mycobacterium tuberculosis 16S rRNA in the presence of 10 ng/µl negative RNA (yeast RNA), the positive signal (detection sensitivity) is markedly increased, and facilitates the determination whether the sample is positive or negative.

It remains to be clarified why EDTA or its salt improves the positive signal, but the reason may be as follows. EDTA, when added to the amplification reaction mixture, prevents the primers from binding to non-target sequences and inhibits non-specific amplification reactions, with the result that the primers and substrates (such as rNTP and dNTP) are prevented from being consumed by the nonspecific reactions, leading to a higher amplification efficiency. Further, since non-specific reaction products are reduced, the signal is less likely to be decreased by the presence of such byproducts. However, it should be noted that the above theory in no way restricts the scope of the invention.

Since the reaction mixture for NASBA usually contains about 12 mM magnesium chloride, the present inventors presumed at first that EDTA or its salt achieves the effect by cheleting action. If the presumption is correct, the same effect must be achieved by controlling the magnesium chloride concentration. Actually, however, the signal decreases when the concentration of magnesium chloride is reduced to less than 12 mM. In view of the above, the effect of the invention can be achieved for other reasons than the change in magnesium ion concentration caused by addition of EDTA or its salt.

Example 2

Mycobacterium tuberculosis 16S rRNA (initial concentration: 10 pg/µl) was amplified and detected in the same manner as in Example 1 except for using EDTA-Na at concentrations shown in Table 2 (0 to 80 mM). As a control test, the amplification reaction was carried out using distilled water in place of Mycobacterium tuberculosis 16S rRNA to test the influence of EDTA-Na on the detection. The results are shown in Table 2, wherein the numeric values indicate luminescence quantities (cps, count/second).

TABLE 2

| EDTA concentration | 10 pg/µl of Mycobacterium RNA | Distilled water |
| --- | --- | --- |
| 80 mM | 75,623 | 86 |
| 60 mM | 142,657 | 64 |
| 40 mM | 132,155 | 72 |
| 20 mM | 129,875 | 68 |
| 10 mM | 135,126 | 95 |
| 5 mM | 146,230 | 82 |

TABLE 2-continued

| EDTA concentration | 10 pg/µl of Mycobacterium RNA | Distilled water |
| --- | --- | --- |
| 3 mM | 120,339 | 59 |
| 0 | 18,546 | 86 |

As apparent from Table 2, addition of EDTA-Na at any concentration (3 to 80 mM) remarkably increases the positive signal, as compared with the positive signal obtained without using EDTA-Na. The results of the control test reveal that the luminescence quantity from the control sample is not increased by addition of EDTA-Na, demonstrating that EDTA-Na does not affect the detection.

Example 3

Amplification of Mycobacterium tuberculosis 16S rRNA using amplification reaction mixture containing NTA, and detection of amplified RNA (1) NASBA of Mycobacterium tuberculosis 16S rRNA Mycobacterium tuberculosis 16S rRNA was amplified using the same reagent and following the same procedure as in Example 1 except for adding NTA-Na, in place of EDTA, to the amplification reaction mixture. The amplified RNA was subjected to sandwich hybridization on a microtiter plate by the method (7) in Example 1 to test the signal enhancing effect of NTA.

(2) Results (effect of addition of NTA-Na in the presence of negative RNA (10 ng/µl yeast RNA))

The results of (1) are shown in Table 3 (n=4), wherein the numeric values indicate the luminescence quantities (cps, count/second).

TABLE 3

| Concentration of Mycobacterium RNA | NTA concentration in reaction mixture for NASBA of Mycobacterium tuberculosis 16S rRNA | | | | |
| --- | --- | --- | --- | --- | --- |
| | 0 | 0.5 mM | 1.0 mM | 1.5 mM | 3.0 mM |
| 10 pg/µl | 18,546 | 39,564 | 86,542 | 102,345 | 96,576 |
| | 18,222 | 35,164 | 77,956 | 98,459 | 82,564 |
| | 15,431 | 32,214 | 67,012 | 85,426 | 81,042 |
| | 12,426 | 28,895 | 59,842 | 82,164 | 65,423 |
| 1 pg/µl | 5,846 | 4,269 | 12,356 | 41,265 | 38,712 |
| | 1,236 | 4,117 | 10,459 | 35,129 | 36,425 |
| | 959 | 3,526 | 8,023 | 34,102 | 32,156 |
| | 454 | 1,956 | 6,516 | 25,614 | 21,678 |
| 0.1 pg/µl | 525 | 91 | 1,256 | 7,056 | 5,124 |
| | 103 | 87 | 265 | 2,310 | 1,126 |
| | 76 | 69 | 88 | 94 | 76 |
| | 69 | 66 | 69 | 86 | 68 |

As apparent from the above results, addition of NTA-Na to the amplification reaction mixture remarkably increases the luminescence quantity (positive signal). That is, addition of 1.5 mM NTA-Na increases the luminescence quantity 4- to 9-fold when the RNA initial concentration is 10 pg/µl, and 5- to 20-fold when the RNA initial concentration is 1 pg/µl, as compared with the luminescence quantity obtained in the absence of NTA. Like EDTA-Na, NTA-Na accomplishes significant effect at a concentration of 0.5 mM, but higher concentrations are preferable, and concentrations about 1.5 mM are optimal. When NASBA is carried out according the invention (in the presence of NTA), the detection limit is about 0.1 pg/µl, indicating that the process of the invention improves the detection sensitivity achieved by conventional NASBA techniques (in the absence of NTA) about tenfold.

Consequently, like EDTA, NTA exhibits remarkable effects of improving the positive signal (detection sensitivity) and giving clear positive/negative results, when added to the reaction mixture for amplification of Mycobacterium tuberculosis 16S rRNA in the presence of 10 ng/μl negative RNA (yeast RNA).

Such effects are achieved presumably for the following reasons. Like EDTA, NTA inhibits non-specific amplification reactions when added to the amplification reaction mixture, so that the primers and substrates (such as rNTP or dNTP) are prevented from being consumed by non-specific reactions, resulting in a higher amplification efficiency. Further, since the non-specific reaction products are reduced, the signal is less likely to be decreased by the presence of such byproducts. However, it should be noted that the above presumption in no way restricts the scope of the invention.

Example 4

Mycobacterium tuberculosis 16S rRNA (initial concentration: 10 pg/μl) was amplified and detected in the same manner as in Example 3 except for using NTA-Na at concentrations shown in Table 4 (0 to 80 mM). As a control test, the amplification reaction was carried out using distilled water in place of Mycobacterium tuberculosis 16S rRNA to test the influence of NTA-Na on the detection. The results are shown in Table 4, wherein the numeric values indicate luminescence quantities (cps, count/second).

TABLE 4

| NTA concentration | 10 pg/μl Mycobacterium RNA | Distilled water |
| --- | --- | --- |
| 80 mM | 33,451 | 78 |
| 60 mM | 70,056 | 69 |
| 40 mM | 73,456 | 84 |
| 20 mM | 88,897 | 88 |
| 10 mM | 86,597 | 64 |
| 5 mM | 91,102 | 82 |
| 3 mM | 96,576 | 56 |
| 0 | 18,546 | 86 |

As apparent from Table 4, addition of NTA-Na at any concentration (3 to 80 mM) significantly improves the positive signal, as compared with the positive signal obtained in the absence of NTA-Na. The results of the control test reveal that the luminescence quantity from the control sample is not increased by addition of NTA-Na, demonstrating that addition of NTA-Na does not affect the detection.

As discussed above, when the compound such as EDTA or NTA is added to a reaction mixture for sequence-specific nucleic acid amplification, non-specific amplification reactions can be very easily inhibited and thus the detection sensitivity and signal of the amplified product are remarkably improved, without altering physical conditions such as temperature. Further, if a non-target RNA is present as a negative RNA in the amplification reaction system, certain types of target nucleic sequences may give reduced signal when amplified by conventional NASBA techniques. However, according to the invention, addition of the compound such as EDTA, NTA and so on can significantly improve the sensitivity without being affected by the negative RNA.

Presumably, EDTA, NTA and other compounds for use in the invention have an action mechanism which inhibits the primers from binding to non-target sequences to thereby prevent mispriming. Accordingly, the nucleic acid amplification process of the invention is applicable in not only NASBA illustrated in Examples, but also other RNA amplification techniques including TMA and 3SR, and DNA amplification techniques including PCR and its modifications, and therefore very valuable as an improvement of these techniques.

What is claimed is:

1. A reagent for nucleic acid amplification comprising a forward primer having a DNA sequence homologous to a sequence of a target RNA; a reverse primer having a DNA sequence complementary to a sequence of the target RNA and having a promoter for RNA polymerase attached to its 5' end; ribonucleotides; deoxyribonucleotides; a reverse transcriptase or RNA directed DNA polymerase; a RNase H; a DNA polymerase or reverse transcriptase having DNA-directed DNA polymerase activity; a RNA polymerase; and at least one member selected from the group consisting of ethylenediamine tetraacetic acid, nitrirotriacetic acid, uramil diacetic acid, trans-1,2-cyclohexanediaminetetraacetic acid, diethylenetriaminepentaacetic acid, ethyleneglycol bis(2-aminoethyl)ether diaminetetraacetic acid, triethylene tetraminehexaacetic acid and a salt thereof, wherein said at least one member is present at a final concentration of from 0.5 to 60 mM in the reaction mixture for nucleic acid amplification.

2. A reagent for nucleic acid amplification according to claim 1 further containing a buffer solution.

3. A reagent for nucleic acid amplification comprising a forward primer having a DNA sequence homologous to a sequence of a target RNA; a reverse primer having a DNA sequence complementary to a sequence of the target RNA and having a promoter for RNA polymerase attached to its 5' end; ribonucleotides; deoxyribonucleotides; a reverse transcriptase or RNA directed DNA polymerase; a RNase H; a DNA polymerase or reverse transcriptase having DNA-directed DNA polymerase activity; a RNA polymerase; and at least one member selected from the group consisting of ethylenediaminetetraacetic acid, nitrirotriacetic acid, and a salt, thereof wherein said at least one member is present at a final concentration of from 0.5 to 60 mM in the reaction mixture for nucleic acid amplification.

4. A process for nucleic acid amplification wherein said amplification is a nucleic acid sequence-based reaction that is carried out in the presence of at least one member selected from the group consisting of ethylenediaminetetraacetic acid, nitrirotriacetic acid, uramil diacetic acid, trans-1,2-cyclohexanediamine-tetraacetic acid, diethylenetriamine-pentaacetic acid, ethyleneglycol bis (2-aminoethyl)ether diaminetetraacetic acid, triethylenetetraaminehexaacetic, and a salt of said at least one member, said at least one member being present at a final concentration of from 0.5 to 60 mM.

5. A process for nucleic acid amplification wherein said amplification is carried out in an amplification reaction mixture containing 0.5 to 60 mM of a final concentration of at least one member selected from the group consisting of ethylenediaminetetraacetic acid, nitrirotriacetic acid, uramil diacetic acid, trans-1,2-cyclohexanediaminetetraacetic acid, diethylenetriaminepentaacetic acid, ethyleneglycol bis (2 aminoethyl)ether diaminetetraacetic acid, triethylenetetraminehexaacetic acid and a salt thereof.

6. A process for nucleic acid amplification wherein said amplification is carried out in the presence of at least one member selected from the group consisting of ethylenediaminetetraacetic acid, nitrirotriacetic acid, and a salt thereof, said at least one member being present at a final concentration of from 0.5 to 60 mM.

7. A reagent kit for amplification/detection of a nucleic acid comprising a reagent for nucleic acid amplification according claim 1 and a reagent for nucleic acid detection containing a detection probe.

8. A reagent kit for amplification and/or detection of a nucleic acid comprising a reagent for nucleic acid amplification containing a final concentration of from 0.5 to 60 mM of at least one member selected from the group consisting of ethylenediaminetetraacetic acid, nitrirotriacetic acid, uramil diacetic acid, trans-1,2cyclohexanediaminetetraacetic acid, diethylenetriaminepentaacetic acid, ethyleneglycol bis(2-aminoethyl)ether diaminetetraacetic acid, triethylenetetraminehexaacetic acid , and a salt thereof; and a reagent for nucleic acid detection containing a detection probe, a capture probe and an enzyme substrate.

9. A reagent kit for amplification/detection of a nucleic acid comprising a reagent for nucleic acid amplification according to claim 1 and a reagent for nucleic acid detection containing a detection probe, a capture probe and an enzyme substrate.

10. A process for nucleic acid amplification comprising amplifying said nucleic acid in the presence of a final concentration of from 0.5 to 60 mM of at least one member selected from the group consisting of ethylenediamineacetic acid, nitrotriacetic acid, uramil diacetic acid, trans-1,2-cyclohexadiamine-tetraacetic, diethylenetriaminepentaacetic acid, ethyleneglycol bis(2-aminoethyl)ether diaminetetraacetic acid, triethylene tetraaminehexaacetic acid, and a salt of said at least one member, using a nucleic acid amplification reaction selected from the group consisting of Nucleic Acid Sequence-Based Amplification (NASBA), transcription Mediated Amplification (TMA), Self Sustained sequence Replication Reaction (3SR) and Strand Displacement Amplification (SDA).

* * * * *